United States Patent
Zamboni et al.

[11] Patent Number: 5,310,884
[45] Date of Patent: May 10, 1994

[54] LTD4 RECEPTOR AND PHOTOAFFINITY PROBE

[75] Inventors: Robert Zamboni, Pointe-Claire; Kathleen M. Metters, Montreal, both of Canada

[73] Assignee: Merck Frosst Canada, Inc., Kirkland, Canada

[21] Appl. No.: 862,692

[22] Filed: Apr. 3, 1992

[51] Int. Cl.$^5$ .................. C07K 3/06; C07K 15/14; C07K 7/00
[52] U.S. Cl. ..................... 530/408; 530/402; 530/395; 530/350; 530/404; 436/504; 436/545; 436/804
[58] Field of Search ............... 530/350, 408, 402, 395, 530/404; 436/504, 545, 804

[56] References Cited
PUBLICATIONS

Mong et al., Mol. Pharmacol 29: 235–243 (1986).
Mong and Sarau, Mol. Pharmacol 37: 60–64 (1990).
Watanabe, J. Biol. Chem. 265: 21237–21241 (1990).

*Primary Examiner*—Michael G. Wityshyn
*Assistant Examiner*—C. Sayala
*Attorney, Agent, or Firm*—Mark R. Daniel; Joseph F. DiPrima

[57] ABSTRACT

The LTD$_4$ receptor has been defined by radioligand binding studies as a member of the family of G-protein coupled receptors. A photoactivable azido derivative of LTD$_4$ ([$^{125}$I]Azido-LTD$_4$) has been synthesized for use as a photoaffinity probe. Photoactivation of ([$^{125}$I]Azido-LTD$_4$ under equilibrium binding conditions revealed the selective radiolabeling of a 45 kDa protein in guinea-pig lung membranes, as visualized by SDS-PAGE and autoradiography.

1 Claim, 13 Drawing Sheets

[$^{125}$I]Azido-LTD$_4$ PHOTOLABELLING

[CaCl$_2$] (mM)

[$^{125}$I]Azido-LTD$_4$ PHOTOLABELLING

[NUCLEOTIDE] (µM)

[$^{125}$I]Azido-LTD$_4$ PHOTOLABELLING

[ MONOVALENT CATION ] (mM)

204,219

MK-571

MK-886

LTD4 RECEPTOR AND PHOTOAFFINITY PROBE

SUMMARY OF THE INVENTION

The invention is the photoaffinity probe ([$^{125}$I])azido-LTD$_4$ and the 45 kD protein, as described herein, which selectively binds thereto.

DETAILED DESCRIPTION

Materials

Guinea pigs were from Charles River; [$^3$H]LTD$_4$ (180 Ci/mmol) was from NEN, Dupont; [$^{125}$I]Azido-LTD$_4$ (2200 Ci/mmol), LTC$_4$, LTD$_4$, LTE$_4$, LTB$_4$, MK-571, MK-886 and ICI 204,219 (L-691,013) were synthesized by the Department of Medicinal Chemistry at the Merck Frosst Centre for Therapeutic Research; E-64, GTPγS, ATPγS and recombinant N-Glycosidase F were from Boehringer Mannheim, L-penicillamine, phenylmethylsulphonyl, leupeptin, pepstatin, L-serine, boric acid were from the Sigma Chemical Company; Rabbit anti-guinea-pig albumin antisera (RAGpAlb) was from Immunological Laboratories; Protein A-Sepharose was from Pharmacia; Octylglucoside was from Calbiochem; Sodium dodecyl sulphate polyacrylamide gel electrophoresis reagents were from Biorad. All other reagents were of analytical grade.

Methods

Guinea-Pig Lung Membrane Preparation

Guinea pigs (male; 350 g) were sacrificed by cervical dislocation and the lung tissues removed. All subsequent procedures were performed either on ice or at 4° C. Connective tissue, trachea, large blood vessels and major airways were dissected away and the remaining lung tissue (primarily parenchyma) was finely minced prior to homogenisation in 10 vol of 10 mM HEPES/KOH pH 7.4, containing 0.25 M sucrose, 2 mM EDTA, 2 mM phenylmethylsulphonyl fluoride, 10 μg/ml pepstatin, 10 μg/ml leupeptin and 10 μM E-64, using 5 s bursts of a polytron (Brinkman Instruments). The homogenate was subjected to differential centrifugation at 1000×g for 10 min, 10,000×g for 10 min and 100,000×g for 40 min. The resulting 100,000×g pellets were resuspended in 10 mM HEPES/KOH pH 7.4, containing 10% (w/v) sucrose, at a final protein concentration of 1–2 mg/ml. This tissue suspension was carefully layered over 10 mM HEPES/KOH pH 7.4 containing 40% (w/v) sucrose in a 3:2 (v/v) ratio. The discontinuous sucrose gradient was centrifuged at 83,000×g for 60 min. The membrane fraction located at the interface of the sucrose gradient layers was recovered, diluted 10-fold in 10 mM HEPES/KOH pH 7.4 and further centrifuged at 150,000×g for 40 min. The final membrane pellets were resuspended in 10 mM HEPES/KOH pH 7.4 at a protein concentration of 2–4 mg/ml and stored at 31 80° C.

Synthesis of [$^{125}$I]Azido-LTD$_4$

[$^{125}$I]Azido-LTD$_4$ was synthesized in two steps as follows: [$^{125}$I]-NHS-ASC was synthesized according to the method of Ji and Ji, 1982, and iodinated by the chloramine-T method of Hunter and Greenwood, 1962. The final reaction mixture was evaporated, resuspended in 200 μl of dioxane and allowed to react with an equal volume of LTD$_4$ (10 mg/ml in phosphate buffer, pH 8) for 4 h at room temperature. The reaction mixture was purified by reverse phase high performance liquid chromatography (RP-HPLC) employing a 8 mm μbondapak RCM cartridge (Waters Assoc.) eluted isocratically at a flow rate of 2 ml/min with a mobile phase comprised of 80:20:0.1:0.0025 (v/v) MeOH: H$_2$O:HOAc: 2-mercaptoethanol, containing 0.5 mM EDTA. The partially purified [$^{125}$I]Azido-LTD$_4$ was re-chromatographed under the same RP-HPLC conditions to give the final product.

Preparation of [$^{125}$I]azido LTD$_4$

To 1 mg of phenol 1 in acetone (100 μL) was added a solution of choramine T (20 μL of a solution of 200 mg in 20 mL acetone) followed by pH 7.8 phosphate buffer (2 g/L, 100 μL). Forty μL of a solution of Na $^{125}$I (5 mc/100 μL) was added. The reaction mixture was stirred for 2 min, quenched with sodium bisulfite (100 μL of a solution of 1 g/20 mL), extracted with toluene (250 μL), and evaporated. The residue was dissolved in dioxane (200 μL) and LTD$_4$ (200 μL of a solution of 10 mg/mL LTD$_4$ in pH 8 phosphate buffer) was added. The reaction mixture was stirred at room temperature for 4 h. The reaction mixture was purified (HPLC) on a Waters 8 mm μbondapak RCM cartridge using 80% MeOH, 20% H$_2$O, 0.1% AcOH, mercaptoethanol (100 μL/4 L solution) and EDTA (700 mg/4 L) as eluant with a flow rate of 2 mL/min. The fractions containing the desired product were evaporated, dissolved in MeOH (300 μL), H$_2$O (100 μL) and AcOH (10 μL) and re-chromatographed using the same eluant to give [$^{125}$I]azido LTD$_4$.

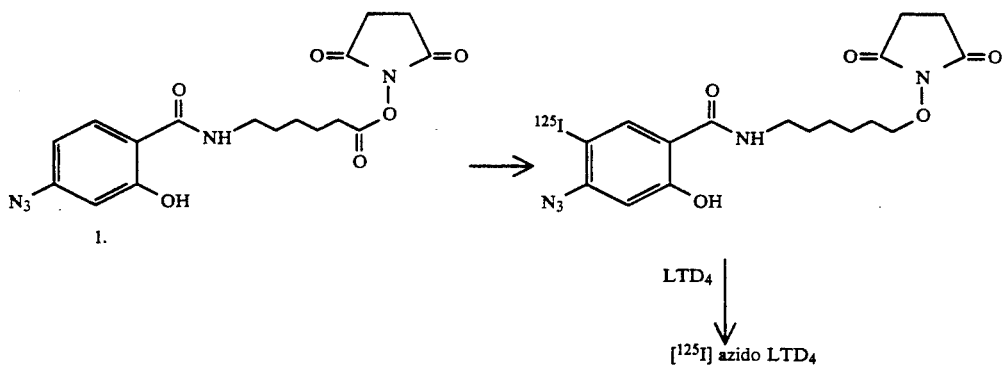

Leukotriene D$_4$ Receptor Binding Assays

[$^{125}$I]Azido-LTD$_4$ binding assays were performed in a final volume of 500 μl of 10 mM HEPES/KOH, pH 7.4, containing 10 mM $CaCl_2$, 60 pM [$^{125}$I]Axido-LTD$_4$ (2200 Ci/mmol) and 20–30 μg of guinea-pig lung membrane protein. When LTC$_4$ was included as competing ligand the incubation medium always contained 50 mM serine-borate to inhibit γ-glutamyl transpeptidase (Tate and Meister, 1978). In all experiments, specific binding was defined as the difference between total binding and non-specific binding determined in the presence of 1 μm LTD$_4$. Incubations were conducted for 60 min at room temperature prior to separation of bound and free [$^{125}$I]Azido-LTD$_4$, by rapid filtration under vacuum through Whatman GF/B filters presoaked at 4° C. in 10 mM HEPES/KOH, pH 7.4, containing 0.01% (w/v) bovine serum albumin. Filters were then washed with 16 ml of 10 mM HEPES/KOH, pH 7.4 containing 0.01% (w/v) bovine serum albumin, at 4° C. Residual [$^{125}$I]Azido-LTD$_4$ bound to the filters was determined by gamma counting (LKB 1272 Clinigamma Quatro counter) with a counting efficiency of approximately 80%. Under these [$^{125}$I]Azido-LTD$_4$ binding assay conditions, the guinea-pig lung membranes bound approximately 10–20% of the [$^{125}$I]Azido-LTD$_4$ added to the incubation. Specific binding was linear with respect to both membrane protein concentration and radioligand concentration and routinely represented 50–60% of the total [$^{125}$I]Azido-LTD$_4$ binding to guinea-pig lung membrane preparations.

[$^3$H]LTD$_4$ binding assays were performed essentially as described for [$^{125}$I]Azido-LTD$_4$ binding assays, except the incubation medium containing 20 mM $CaCl_2$, 200 pM [$^3$H]LTD$_4$ (180 Ci/mmol) and 20 mM of the peptidase inhibitor L-penicillamine (Metters et al., 1991). Following fitration, the residual [$^3$H]LTD$_4$ bound to the filters was determined by liquid scintillation counting in 5 ml Biofluor (NEN) with a counting efficiency of approximately 50%.

Reverse Phase High Performance Liquid Chromatography

RP-HPLC was conducted to assess the stability of [$^{125}$I]Azido-LTD$_4$ under binding assay conditions. Receptor binding assays were performed in a final incubation volume of 1 ml of 10 mM HEPES/KOH, pH 7.4, containing 10 mM $CaCl_2$, 60 pM [$^{125}$I]Azido-LTD$_4$ and 100 μg guinea-pig lung membrane. Following a 60 min incubation at room temperature, samples were centrifuged at 150,000×g for 15 min at 4° C. The supernatant (unbound radioligand) was removed and the membrane pellet was resuspended by sonication in 150 μl of RP-HPLC solvent (77:33:0.1 (v/v) MeOH:H2O:HOAc containing 0.01% 2-mercaptoethanol and 0.5 mM EDTA). The samples were centrifuged at 150,000×g for 15 min at 4° C. and the supernatent removed (bound radioligand). Bound and unbound radioligand fractions (100 μl) were analysed by RP-HPLC using a Nova Pac C$_{18}$ column (0.39 ×15 cm; Waters Assoc.) eluted isocratically at a flow rate of 1 ml/min with RP-HPLC solvent. The profile of iodinated material from bound and unbound radioligand samples was determined by on-line solid scintillation gamma counting (Berthold HPLC radioactivity monitor LB 506 C1). [$^{125}$I]Azido-LTD$_4$ was identified by c0-co-coelution of non-radioactive [$^{127}$I]Azido-LTD$_4$ monitored by optical density at 280 nm.

Photoaffinity Labelling of Guinea-pig Lung Membranes by [$^{125}$I]Azido-LTD$_4$ Photoaffinity labelling of guinea-pig lung membranes by [$^{125}$I]Azido-LTD$_4$ was conducted under equilibrium binding assay conditions. [$^{125}$I]Azido-LTD$_4$ binding assays were performed in a final volume of 2.25 ml of 10 mM HEPES/KOH, pH 7.4, containing 10 mM $CaCl_2$, 60 pM [$^{125}$I]Azido-LTD$_4$ and 40-60 μg/ml of guinea-pig lung membrane protein. Non-specific binding was routinely determined in the presence of 1 μM LTD$_4$. Samples were incubated for 60 min at room temperature. Aliquots (2×500 μl) were then removed and the bound [$^{125}$I]Azido-LTD$_4$ quantified as described for the filtration binding assays. The residual samples were then transferred to 25 mm diameter cluster plate well for photolysis. The cluster plates were placed on aluminium blocks, pre-cooled to −20° C., and illuminated from above with a 40 W ultraviolet light source (Philips, $\gamma_{max}$=350 nm) at a distance of 10 cm for 2 min. The guinea-pig lung membranes were then recovered from 1 ml sample aliquots by centrifugation at 150,000×g for 15 min at 4° C. and solubilized in sodium dodecyl sulphate polyacrylamide gel electrophoresis (SDS-PAGE) sample buffer prior to resolution of the proteins by SDS-PAGE (Laemmli, 1970). Protein bands were visualized by Coomassie Blue staining while radiolabelled proteins were identified by autoradiography of dried gels and quantified by laser densitometry (Molecular Dynamics, ImageQuant).

Immunoprecipitation of [$^{125}$I]Azido-LTD$_4$ Labelled Guinea-pig Lung Membrane Proteins With Rabbit Anti-guinea-pig Albumin Antisera (RAGpAlb)

Photoaffinity labelled guinea-pig lung membranes were prepared as described in the Methods and then solubilized by incubation for 30 min at 4° C. in TXIP buffer consisting of 10 mM Tris/HCl pH 7.2, containing 1% (v/v) Triton X100 and 0.3% (w/v) NaCl. The TXIP solubilized samples were centrifuged at 14,000×g for 15 min at 4° C. and the supernatant mixed directly with 50 μl of non-immune rabbit serum or RAGpAlb premixed for 15 min at 4° C. with 80 μl of protein A-Sepharose (50 mg/ml in TXIP). The samples were incubated for a further 60 min at 4° C., the Sepharose beads were harvested by pulse centrifugation and the pellets then washed with 3×1 ml of TXIP and 3×1 ml of 10 mM Tris/HCl pH 7.4. The final immunocomplex was dissociated by resuspension in SDS-PAGE sample buffer for 5 min at 95° C. and analysed by SDS-PAGE and autoradiography of the dried gels.

Protein Determination

Protein determinations were conducted using the Pierce BCA reagent kit with bovine serum albumin as standard.

BRIEF DESCRIPTION OF THE DRAWINGS

FIG. 2(A) shows the retention time of the [$^{127}$I]Azido-LTD$_4$ standard and FIG. 2(B) shows the profile of the unbound [$^{125}$I]Azido-LTD$_4$ fraction following incubation with guinea-pig lung membrane.

FIG. 5(A) shows the modulation of [$^3$H]LTD$_4$ specific binding by CaCl$_2$ ( ). FIG. 5(B) shows modulation of both [$^{125}$I]Azido-LTD$_4$ specific binding (○) and the selective radiolabelling of the 45 kDa protein ( ) by CaCl$_2$. The total and non-specific radiolabelling of the 45 kDa protein, determined in the absence and presence of 1 μM LTD$_4$, was quantified by laser densitometry. Results are expressed as percentage of maximum specific binding as a function of CaCl$_2$ concentration. FIG. 5(C) shows the radiolabelling of the 45 kDa protein as visualized by SDS-PAGE followed by autoradiography. Only the results for total binding are shown. The radiolabelled 45 kDa protein was not detectable in any of the corresponding non-specific binding incubations (data not shown). These are representative data from two experiments giving similar values.

FIG. 6(A) shows the modulation of [$^3$H]LTD$_4$ specific binding by GTPγS ( )and ATPγS . FIG. 6(B) shows modulation of both [$^{125}$I]Azido-LTD$_4$ specific binding and the selective radiolabelling of the 45 kDa protein by GTPγS ( , ) and ATPγS (Δ, ○). The total and non-specific radiolabelling of the 45 kDa protein, determined in the absence and presence of 1 μM LTD4, was quantified by laser densitometry. Results are expressed as percentage of maximum specific binding as a function of nucleotide concentration. FIG. 6(C) shows the radiolabelling of the 45 kDa protein in the presence of both GTPγS abd APT-γS, as visualized by SDS-PAGE followed by autoradiography. Only the results for total binding are shown. The radiolabelled 45 kDa protein was not detectable in any of the corresponding non-specific binding incubations (data not shown). These are representative data from two experiments giving similar values.

FIG. 7(A) shows the modulation of [$^3$H]LTD$_4$ specific binding by NaCl ( ) and KCl ( ). FIG. 7(B) shows modulation of both [$^{125}$I]Azido-LTD$_4$ specific binding and the selective radiolabelling 45 kDa protein by NaCl ( , ) and KCl (Δ, ○). The total and non-specific radiolabelling of the 45 kDa protein, determined in the absence and presence of 1 μM LTD4, was quantified by laser densitometry. Results are expressed as percentage of maximum specific binding as a function of cation concentration. FIG. 7(C) shows the radiolabelling of the 45 kDa protein in the presence of both NaCl and KCl, as visualized by SDS-PAGE followed by autoradiography. Only the results for total binding are shown. The radiolabelled 45 kDa protein was not detectable in any of the corresponding non-specific binding incubations (data not shown). These are representative data from two experiments giving similar values.

FIG. 8(C) shows the inhibition of the selective radiolabelling of the 45 kDa protein by leukotrienes, with IC$_{50}$ values determined by laser densitometry. These are representative data from two experiments giving similar values.

FIG. 9(C) shows the inhibition of the selective radiolabelling of the 45 kDa protein by leukotriene-receptor antagonists, with IC$_{50}$ values determined by laser densitometry. These are representative data from two experiments giving similar values.

RESULTS

[$^{125}$I]Azido-LTD$_4$ as a specific ligand for the leukotriene D$_4$ receptor in guinea-pig lung membranes

Figure 1A:
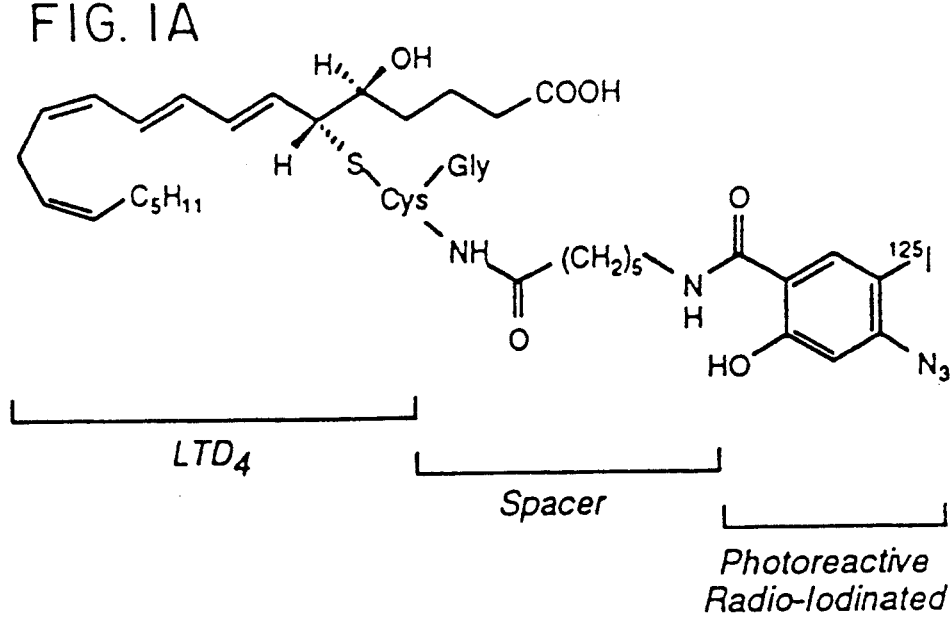
FIG. 1(A) Structure of Iodinated Azido-LTD$_4$ and FIG. 1(B) Competition for [$^3$H]LTD$_4$ specific binding to guinea-pig lung membranes by [$^{127}$I]Azido-LTD$_4$. [$^3$H]LTD$_4$ binding assays were performed as described in the Methods in the presence of 0.01–100 nM LTD$_4$ ( ) and [$^{127}$I]Azido-LTD$_4$ (◯). Competition experiments were analysed and IC$_{50}$ values derived using the Kinetic, EBDA, Ligand, Lowry program from Biosoft (McPherson, 1985). The corresponding K$_i$ values were derived from the equation $K_i = IC_{50}/1 + (L/K_D)$ where $K_i$ is equal to the apparent equilibrium dissociation constant of the unlabeled competing ligand, $K_D$ is equal to the equilibrium dissociation constant of the radioligand, $IC_{50}$ equals the concentration of unlabeled competing ligand that inhibits 50% of radioligand binding and L is equal to the concentration of free radioligand.
Figure 1B:
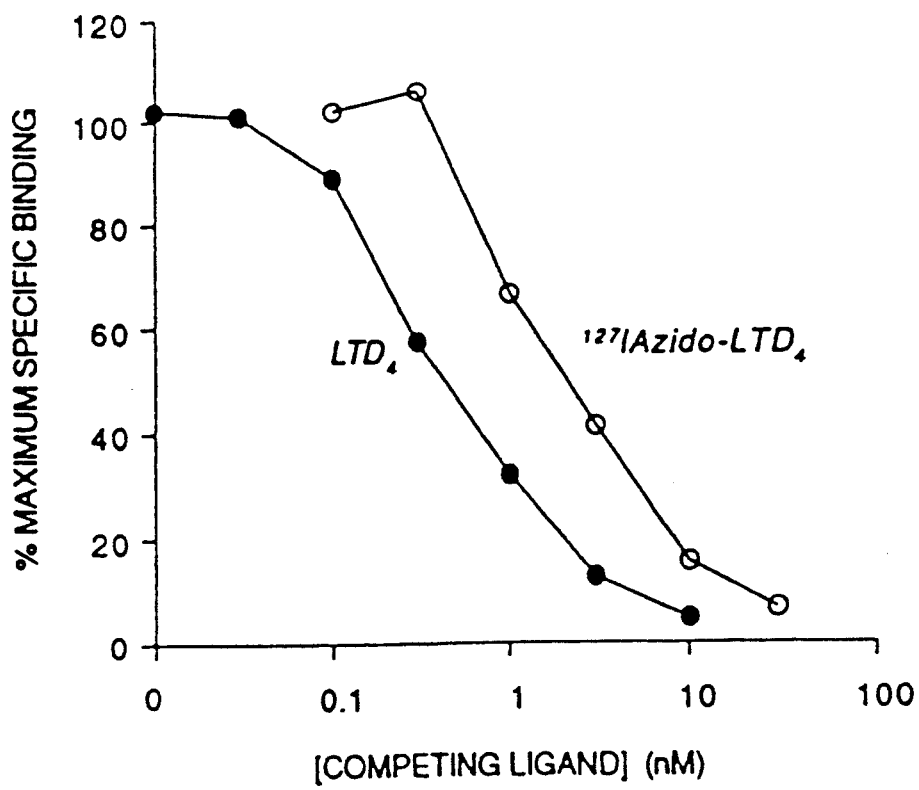

[$^{125}$I]Azido-LTD$_4$ and the non-radioactive analogue [$^{127}$I]Azido-LTD$_4$ were synthesized and purified by essentially the same procedure, as described in the Methods. The ligand is comprised of a photoactivatable iodinated aryl azide coupled via a spacer arm to the α-amino group of the cysteine residue of LTD$_4$, as shown in FIG. 1A. In a preliminary Study, non-radioactive [$^{127}$I]Azido-LTD$_4$ was found to be a potent competing ligand for [$^3$H]LTD$_4$ specific binding to guinea-pig lung membranes, with a K$_i$ value of 1.7 nM (n=2), only 5-fold higher than the K$_i$ of 0.33 nM (n=2) obtained for LTD$_4$ in the same assay, FIG. 1B. This result showed that the LTD$_4$ analogue, [$^{127}$I]Azido-LTD$_4$, retained high affinity for the LTD$_4$ receptor. [$^{125}$I]Azido-LTD$_4$ was then prepared and the binding characteristics of this radioligand were studies employing a [$^{125}$I]Azido-LTD$_4$ radioreceptor binding assay.

Figures 2A, 2B:
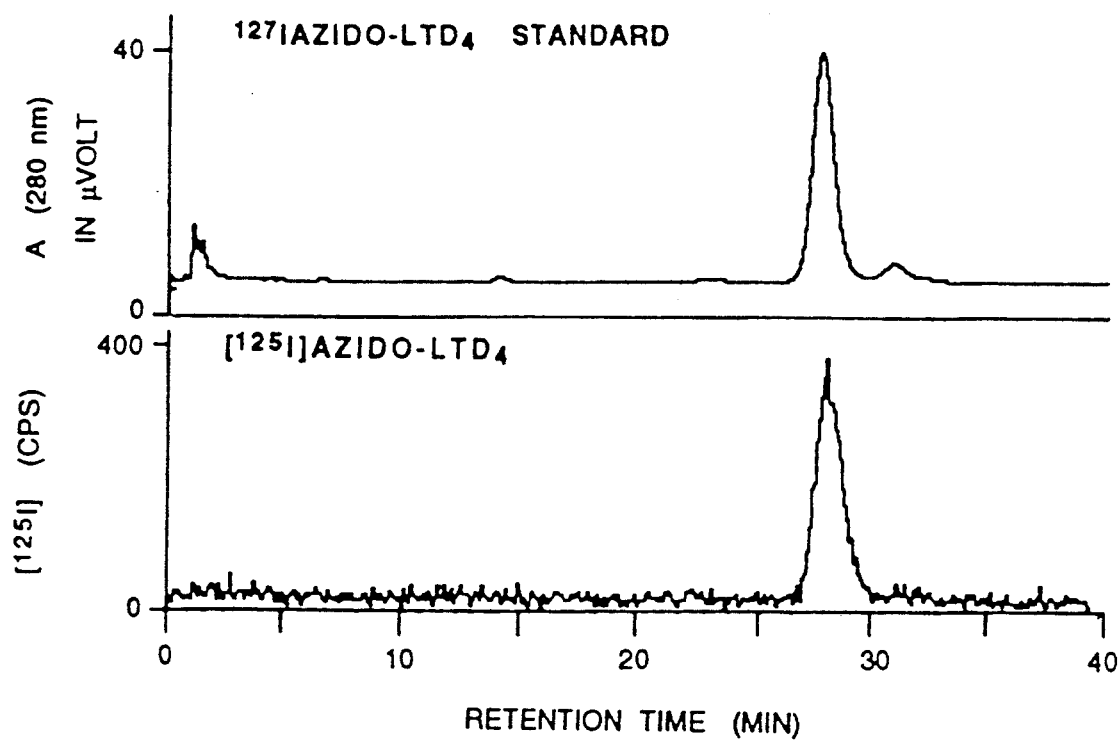
FIGS. 2(A) and 2(B) RP-HPLC analysis of [$^{125}$I]Azido-LTD$_4$ stability. RP-HPLC was used to assess the stability of [$^{125}$I]Azido-LDT$_4$ under the conditions routinely employed for binding assays as described in the Methods.

As an initial step in establishing the [$^{125}$I]Azido-LTD$_4$ binding assay, the stability of the radioligand during incubation with guinea-pig lung membrane proteins, under standard [$^{125}$I]Azido-LTD$_4$ binding assay conditions, was confirmed. Bound and abound radioligand fractions were separated by centrifugation and the profile of radiolabeled material analysed by RP-HPLC. The same results were obtained for both bound and unbound fractions, with RP-HPLC revealing a single peak of radioactivity co-eluting with the [$^{127}$I]Azido-LTD$_4$ standard at a retention time of 29 min, FIG. 2(A)–2(B). The recovery of radioactive material following RP-HPLC was approximately 100%. These data confirmed that [$^{125}$I]Azido-LTD$_4$ was completely stable under the experimental conditions.

Figure 3:
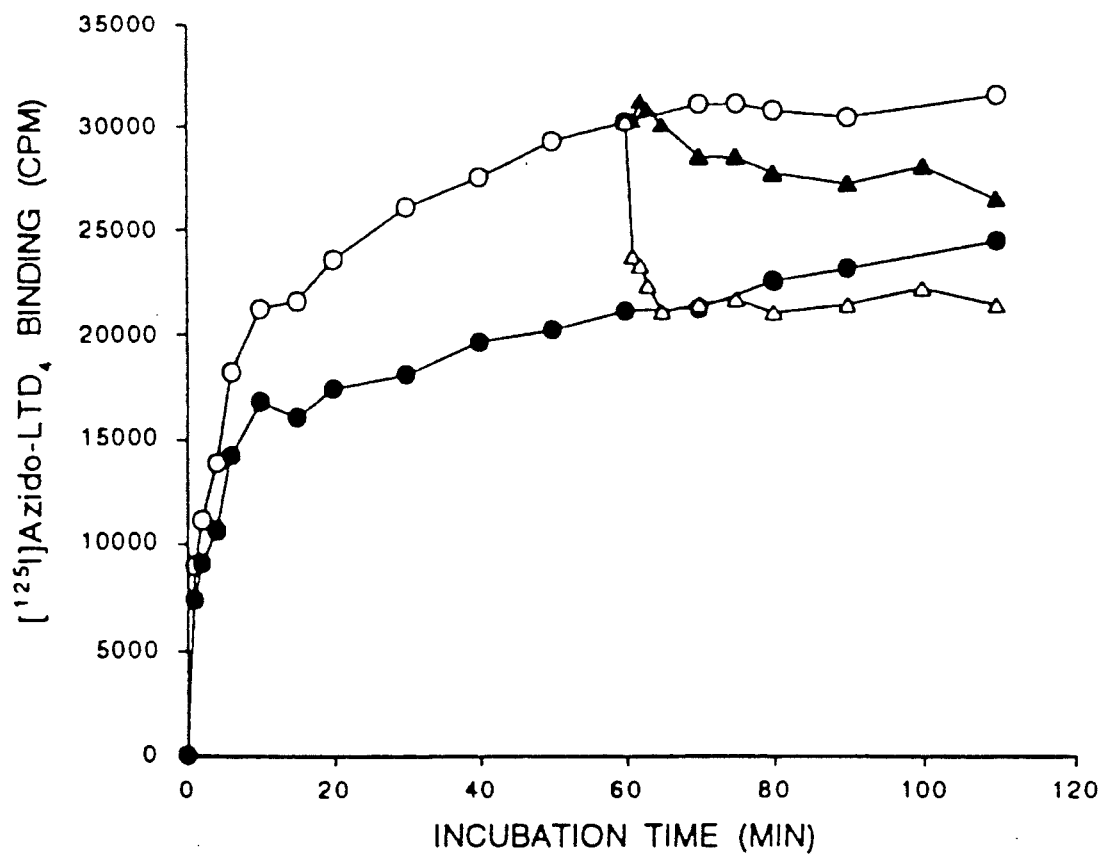
FIG. 3. Rates of association and dissociation of [$^{125}$I]Azido-LTD$_4$ binding to guinea-pig lung membranes. The rate of association and dissociation of total (○) and non-specific ( ) binding were monitored by sampling from homogeneous [$^{125}$I]Azido-LTD$_4$ binding incubations of 24 ml and 10 ml, respectively. Incubations were performed in the absence (○) and presence ( ) of 1 μM LTD$_4$. Aliquots (500 μl) were removed and filtered at the required time intervals. After 60 min the rate of dissociation of total binding was monitored, by sampling, following the addition of either 1 μM LTD$_4$ ( ) or 1 μM LTD$_4$ (Δ) with 10 μM GTP-γS.

Several fundamental criteria for [$^{125}$I]Azido-LTD$_4$ binding specifically to the LTD$_4$ receptor were then examined. The rate of association of [$^{125}$I]Azido-LTD$_4$ binding to guinea-pig lung membranes was slow, reaching equilibrium over a 60 min incubation period, FIG. 3. The addition of 1 μM LTD$_4$ (>1000-fold excess) upon establishment of equilibrium caused a partial dissociation of the [$^{125}$I]Azido-LTD$_4$ binding, approximately 50% over the additional 50 min incubation time. However, the inclusion of 10 μM GTPγS with the competing LTD$_4$ resulted in an almost instantaneous and complete dissociation of [$^{125}$I]Azido-LTD$_4$ binding to non-specific levels. This profile is identical to that obtained for the association and dissociation of [$^3$H]LTD$_4$ binding to guinea-pig lung membranes under identical experimental conditions (data not shown).

[$^{125}$I]Azido-LTD$_4$ specific binding to guinea-pig membranes was saturable, as demonstrated by incubating tissue with an increasing concentration of radioligand (2–200 pM) in the absence and presence of 1 μM LTD$_4$. Linear transformation of the deduced specific binding saturation curve by Scatchard plot analysis showed that [$^{125}$I]Azido-LTD$_4$ specific binding conformed to a single site model, with an equilibrium dissociation constant (K$_D$) of 0.2 nM and a maximum number of binding sites (B$_{max}$) of 1000 fmol/mg protein. Scatchard plot analysis of [$^3$H]LTD$_4$ specific binding saturation data obtained under the same experimental conditions gave comparable results, a gain revealing a single population of binding sites, with a K$_D$ of 0.1 nM and a B$_{max}$ of 2000 fmol/mg protein.

These data support the proposal that [$^{125}$I]Azido-LTD$_4$ binds with high affinity to a G-protein coupled LTD$_4$ receptor in guinea-pig lung membranes.

Photoaffinity Labelling of Guinea-Pig Lung Membranes by [$^{125}$I]Azido-LTD$_4$

Figure 4:
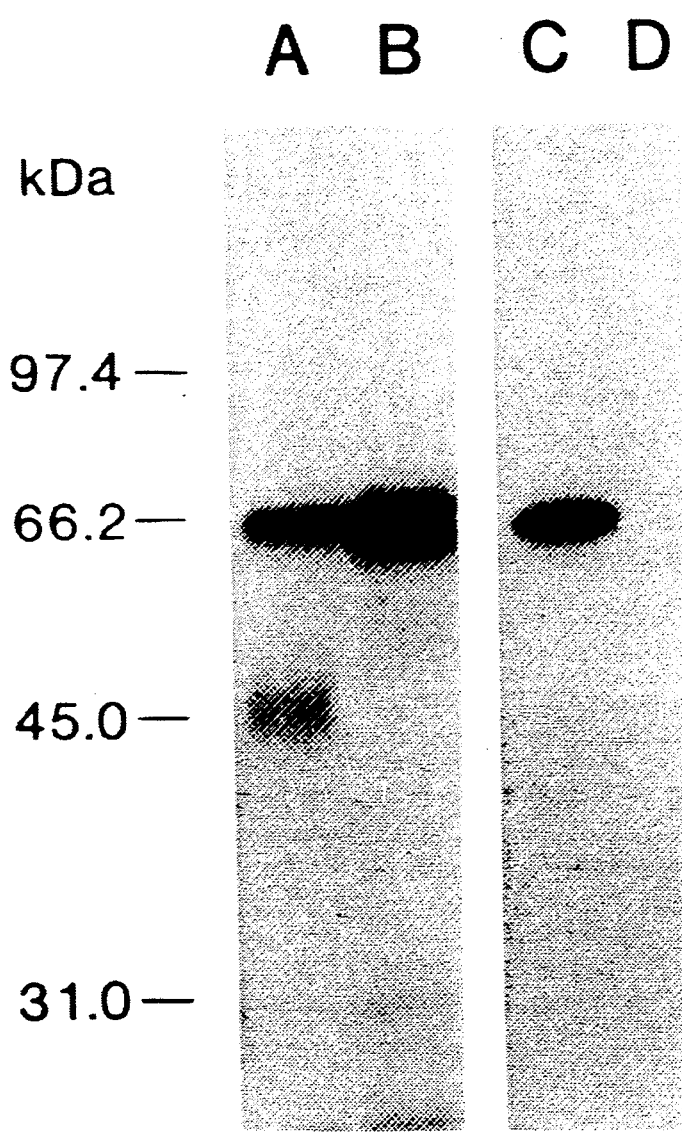
FIG. 4. Photoaffinity labelling of guinea-pig lung membranes by [$^{125}$I]Azido-LTD$_4$ and immunoprecipitation of [$^{125}$I]Azido-LTD$_4$ labelled proteins with rabbit anti-guinea-pig albumin antisera (RAGpAlb). Photoaffinity labelling of guinea-pig lung membranes by [$^{125}$I]Azido-LTD$_4$ was performed under equilibrium binding assay conditions, as described in the Methods. Radiolabelled proteins were resolved by SDS-PAGE and visualized by autoradiography. The profile of [$^{125}$I]Azido-LTD$_4$ photoaffinity labelled proteins obtained following photolysis of binding assays performed in the absence (Lane A) and presence (Lane B) of 1 μM LTD$_4$ is shown in FIG. 4. In addition, photoaffinity labelled membranes were subjected to immunoprecipitation with RAGpAlb (Lane C) and non-immune rabbit serum (Lane D), as described in the Methods. The migration of molecular weight standards is indicated on the left.

[$^{125}$I]Azido-LTD$_4$ was incubated with guinea-pig lung membranes, under standard equilibrium binding assay conditions, in the absence and presence of 1 μM LTD$_4$ to assess total and non-specific binding. Filtration of control samples confirmed that [$^{125}$I]Azido-LTD$_4$ specific binding accounted for approximately 50% of the total [$^{125}$I]Azido-LTD$_4$ binding to the guinea-pig lung membranes at the end of the 60 min incubation. The samples were then subjected to photolysis and processed as described in the Methods. Visualization of [$^{125}$I]Azido-LTD$_4$ photoaffinity labelled proteins by SDS-PAGE and autoradiography revealed two prominent radiolabelled proteins migrating with apparent molecular weights of 66,200 and 45,000, FIG. 4 Lane A. However, only the radiolabelling of the 45 kDa protein was selectively completed for by excess LTD$_4$, under the experimental conditions used to determined non-specific binding, FIG. 4 Lane B. Therefore the 45 kDa protein exclusively was considered a candiate for representing radiolabeled LTD$_4$ receptor.

The 66.2 kDa protein was found to co-migrate with the bovine albumin molecular weight standard during SDS-PAGE. Therefore, the possibility that [$^{125}$I]Azido-LTD$_4$ non-specifically radiolabelling guinea-pig albumin present in the guinea-pig lung membrane preparations was investigated, FIG. 4. Photoaffinity labelled membranes were solubilized and treated with either rabbit anti-guinea-pig albumin antisers (RAGpAlb) or rabbit non-immune serum. In the untreated control the radiolabelled 66.2 kDa and 45 kDa proteins were clearly visible, Lane A. Treatment with RAGpAlb resulted in the specific immunoprecipitation of the 66.2 kDa protein, FIG. 4 Lane C, whereas treatment with non-immune rabbit serum failed to immunoprecipitate any radiolabelled material, FIG. 4 Lane D. In parallel experiments guinea-pig serum was incubated with [$^{125}$I]Azido-LTD$_4$ under standard equilibrium binding assay conditions. The samples were then subjected to photolysis. Analysis of the serum proteins by SDS-PAGE and autoradiography once again revealed the radiolabelling of a 66.2 kDa protein which co-migrated with bovine serum albumin standard (data not shown). Taken together, these data identify the 66.2 kDa protein, non-selectively labelled by [$^{125}$I]Azido-LTD$_4$, as guinea-pig serum albumin.

Figure 5A:
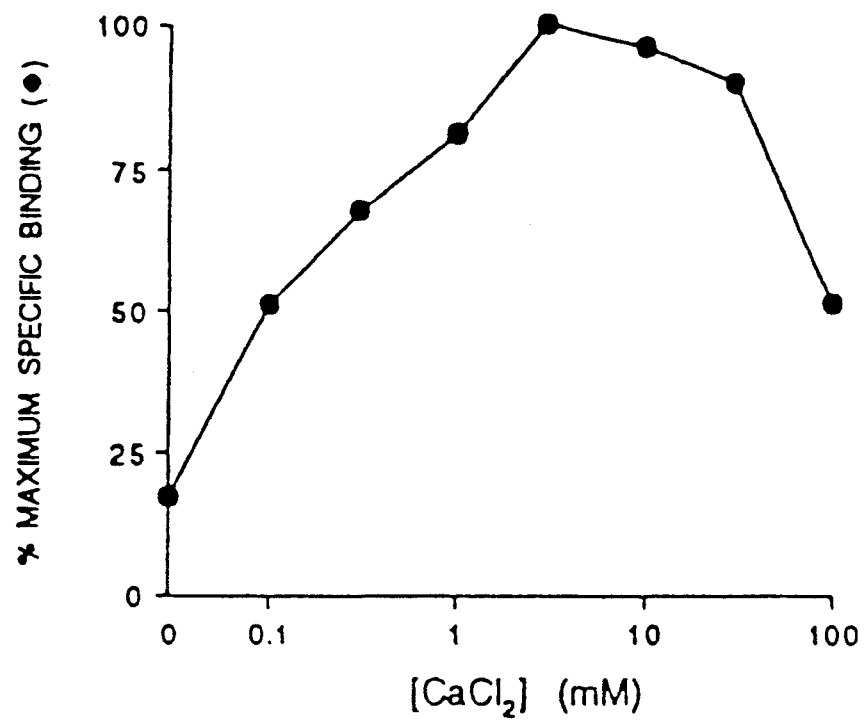
FIGS. 5(A)-5(C). Enhancement of [$^3$H]LTD$_4$ and [$^{125}$I]Azido-LTD$_4$ specific binding and [$^{125}$I]Azido-LTD$_4$ photolabelling of the 45 kDa protein by CaCl$_2$. [3H]LTD$_4$ and [$^{125}$I]Azido-LTD$_4$ binding assays and [$^{125}$I]Azido-LTD$_4$ photoaffinity labelling of guinea-pig lung membranes were performed, as described in the Methods, in the presence of 0-100 mM CaCl$_2$.
Figure 5B:
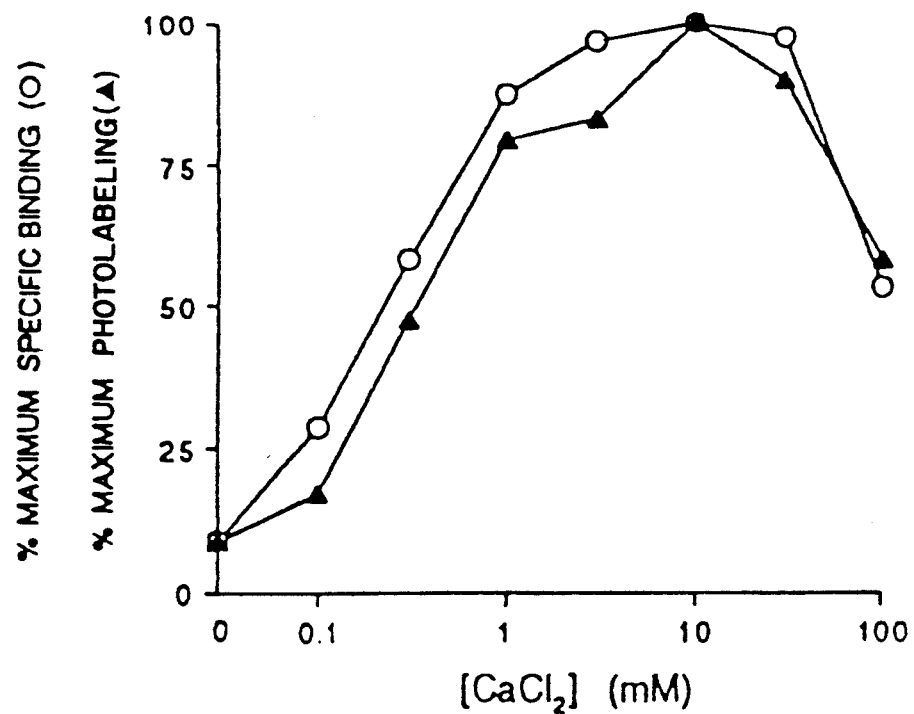
Figure 5C:
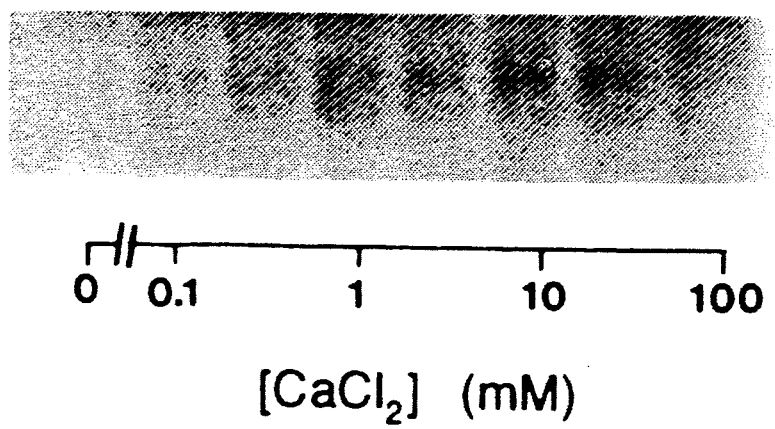

Photoaffinity Labelling of the 45 kDa Guinea-Pig Lung Membrane Protein by [$^{125}$I]Azido-LTD$_4$: Enhancement by Divalent Cations The specific binding of both [$^3$H]LTD$_4$ and [$^{125}$I]Azido-LTD$_4$ to guinea-pig lung membranes was markedly enhanced in the presence of CaCl$_2$, FIGS. 5(A) and 5(B). In both cases, specific binding of the radioligand to guinea-pig lung membranes was increases 5–10 fold over a cation concentration range up to 30 mM, with higher concentrations proving inhibitory. Optimal specific binding was observed at between 3–30 mM CaCl$_2$. The selective [$^{125}$I]Azido-LTD$_4$ photolabelling of the 45 kDa guinea-pig lung protein was also enhanced by CaCal$_2$, in a parallel manner, over the same concentration range. Optimal radiolabelling was again obtained between 3–30 mM CaCl$_2$, FIG. 5(B). The CaCl$_2$ dependent radiolabelling of the 45 kDa protein following photolysis of binding incubations is shown in FIG. 5(C). These data show that the selective [$^{125}$I]Azido-LTD$_4$ photolabelling of the 45 kDa guinea-pig lung membrane protein, and both [$^3$H]LTD$_4$ and [$^{125}$I]Azido-LTD$_4$ specific binding to these membranes, are modulated in the same manner by the presence of CaCl$_2$ in equilibrium binding assay incubations. Identical results were observed using MgCl$_2$ instead of CaCl$_2$, confirming that this is a general divalent cation effect.

Figure 6C:
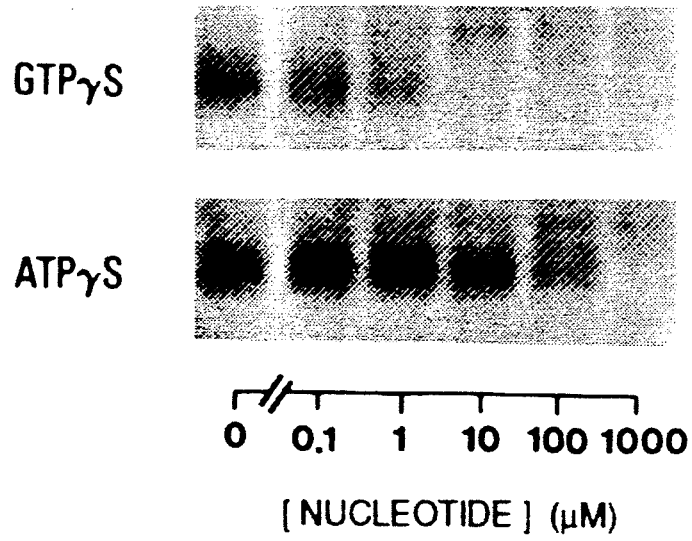
FIGS. 6(A)-6(C) Inhibition of [$^3$H]LTD$_4$ and [$^{125}$I]Azido-LTD$_4$ specific binding and [$^{125}$I]Azido-LTD$_4$ photolabelling of the 45 kDa protein by nucleotide analogues. [$^3$H]LTD$_4$ and [$^{125}$I]Azido-LTD$_4$ binding assays and [$^{125}$I]Azido-LTD$_4$ photoaffinity labelling of guinea-pig lung membranes were performed, as described in the Methods, in the presence of 0-100 μM GTPγS and ATPγS.
Figure 6A:
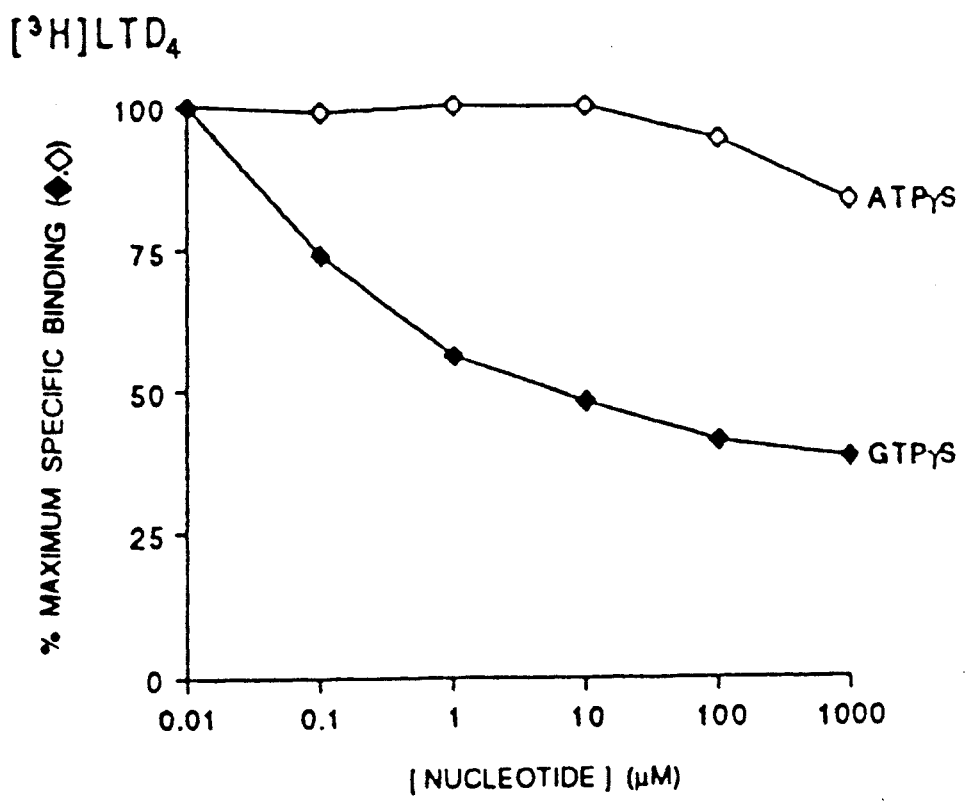
Figure 6B:
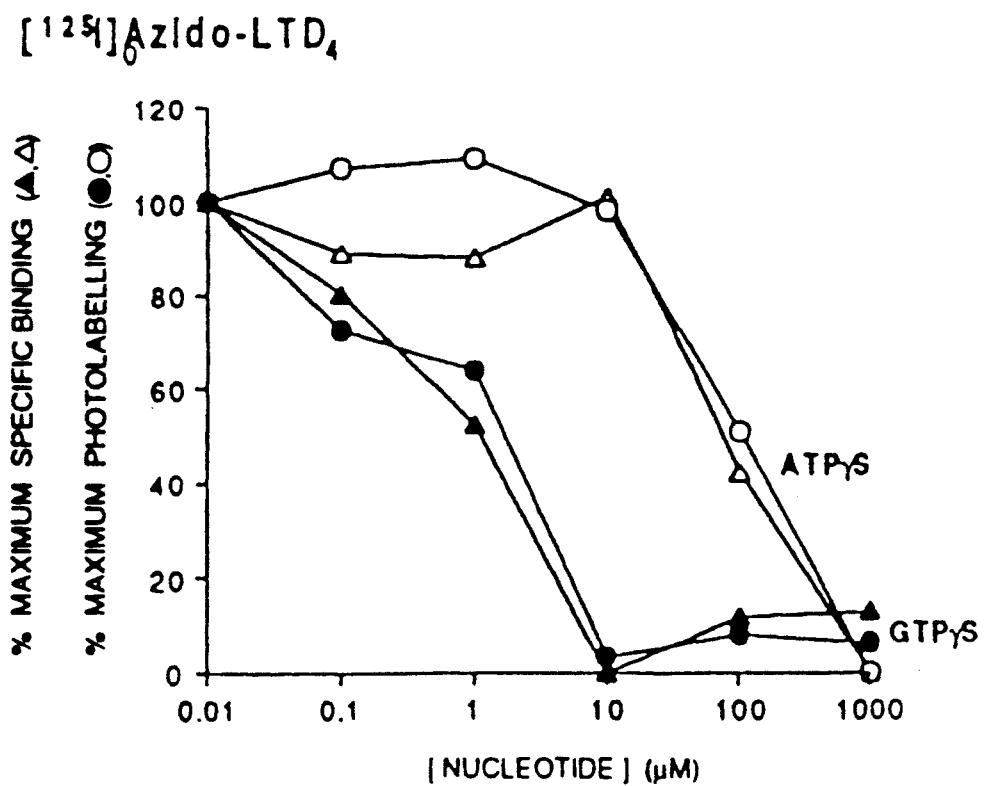

Photoaffinity Labelling of the 45 kDa Guinea-Pig Lung Membrane Protein by [$^{125}$I]Azido-LTD$_4$: Inhibition by Nucleotide Analogues and Sodium Ions The non-hydrolysable GTP analogue, GTP$\gamma$S, inhibited both [$^3$H]LTD$_4$ and [$^{125}$I]Azido-LTD$_4$ LTD$_4$ specific binding to guinea-pig lung membranes with IC$_{50}$ values of 10 $\mu$M and 1 $\mu$M, respectively, FIGS. 6(A) and 6(B). [$^{125}$I]Azido-LTD$_4$ specific binding proved especially sensitive to modulation by GTP analogue, with complete inhibition achieved at 10 $\mu$M GTP$\gamma$S. In contrast, only 60% inhibiton of [$^3$H]LTD$_4$ specific binding using 1000 $\mu$M GTP$\gamma$S, the highest analogue concentration tested. However, the inhibiton of both [$^3$H]LTD$_4$ and [$^{125}$I]Azido-LTD$_4$ specific binding to guinea-pig membranes was selective for GTP$\gamma$S, since ATP$\gamma$S had no detectable effect on [$^3$H]LTD$_4$ specific binding and was 100-fold less potent in inhibiting [$^{125}$I]Azido-LTD$_4$ specific binding, FIGS. 6(A) and 6(B). The selective [$^{125}$I]Azido-LTD$_4$ photolabelling of the 45 kDa guinea-pig lung membrane protein was also inhibited by both nucleotide analogues in a concentration dependent manner, FIG. 6(B). GTP$\gamma$S was again 100-fold more potent than ATP$\gamma$S, displaying an IC$_{50}$ value of 1 $\mu$M, identical to the IC$_{50}$ value obtained for GTP$\gamma$S inhibition of [$^{125}$I]Azido-LTD$_4$ specific binding. The nucleotide-dependent inhibition of the radiolabelling of the 45 kDa protein following photolysis of binding incubations is shown in the autoradiograph in FIG. 6(C). These results confirm that GTP$\gamma$S and ATP$\gamma$S inhibit both [$^{125}$I]Azido-LTD$_4$ specific binding to guinea-pig lung membranes and the selective [$^{125}$I]Azido-LTD$_4$ photolabelling of the 45 kDa protein in this tissue in a comparable manner. This inhibition profile is also in agreement with the effect of GTP$\gamma$S and ATP$\gamma$S on [$^3$H]LTD$_4$ specific binding in these preparations.

Figure 7A:
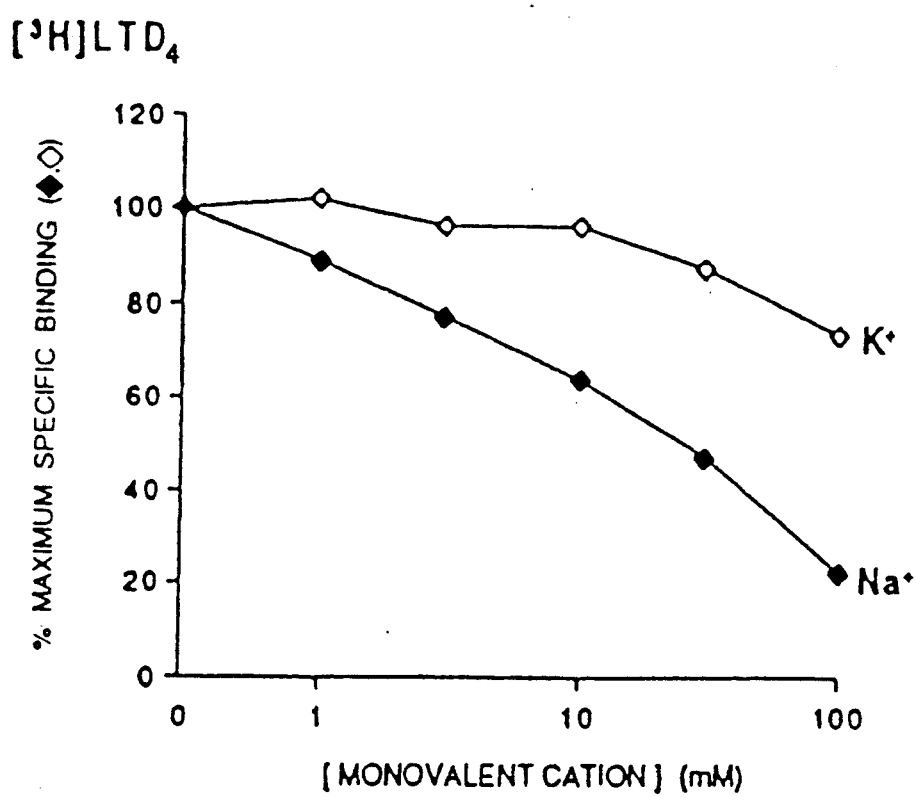
FIGS. 7(A)-7(C) Inhibition of [$^3$H]LTD$_4$ and [$^{125}$I]Azido-LTD$_4$ specific binding and [$^{125}$I]Azido-LTD$_4$ photolabelling of the 45 kDa protein by monobalent cations. [$^3$H]LTD$_4$ and [$^{125}$I]Azido-LTD$_4$ binding assays and [$^{125}$I]Azido-LTD$_4$ photoaffinity labelling of guinea-pig lung membranes were performed, as described in the Methods, in the presence of 0-100 mM NaCl and KCl.
Figure 7B:
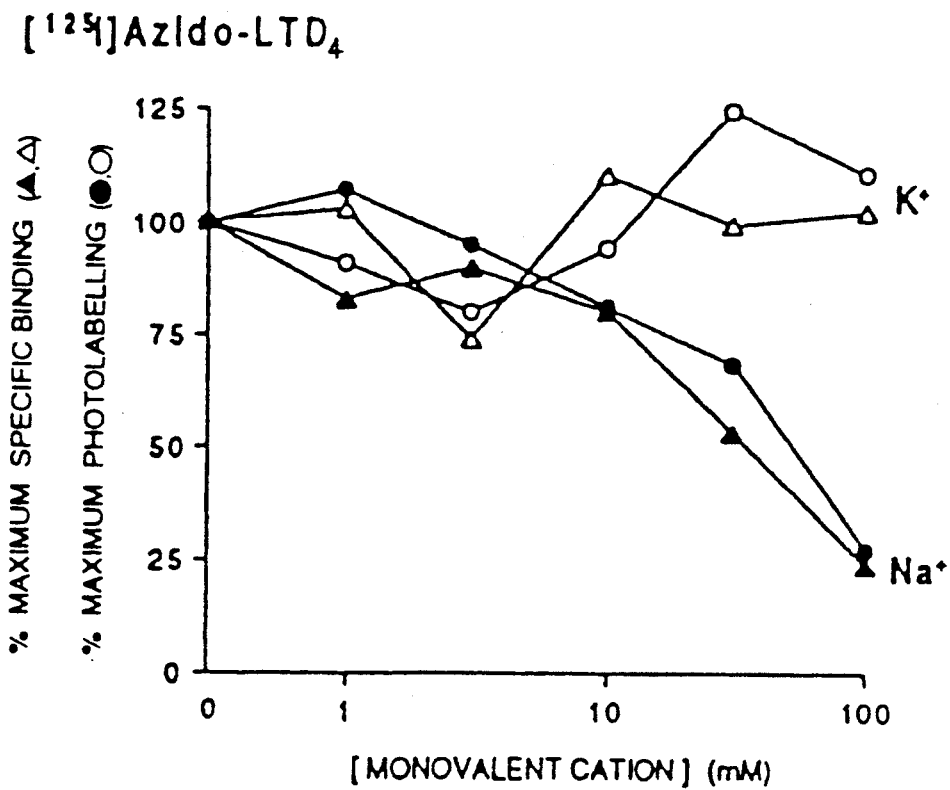
Figure 7C:
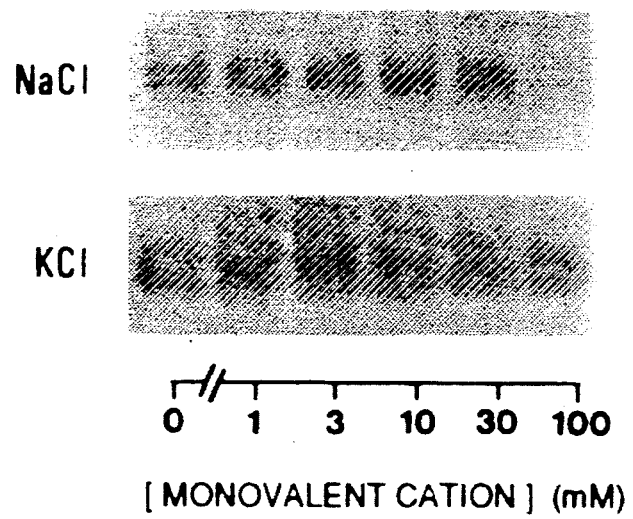

Similar results were obtained in studies evaluating the effect of the monovalent cations. NaCl inhibited both [$^3$H]LTD$_4$ and [$^{125}$I]Azido-LTD$_4$ specific binding to guinea-pig lung membranes, with an IC$_{50}$ value of approximately 30 mM in both cases, FIGS. 7(A) and 7(B). The selective radiolabelling of the 45 kDa guinea-pig lung membrane protein was also inhibited in a concentration dependent manner by NaCl, again with an IC$_{50}$ value of approximately 30 mM, FIGS. 7(A) and 7(B). This effect was shown to be specific for sodium ions since KCl did not significantly inhibit either specific binding or photolabelling, over the same cation concentration range, FIGS. 7(A), 7(B) and 7(C).

Figure 8C:
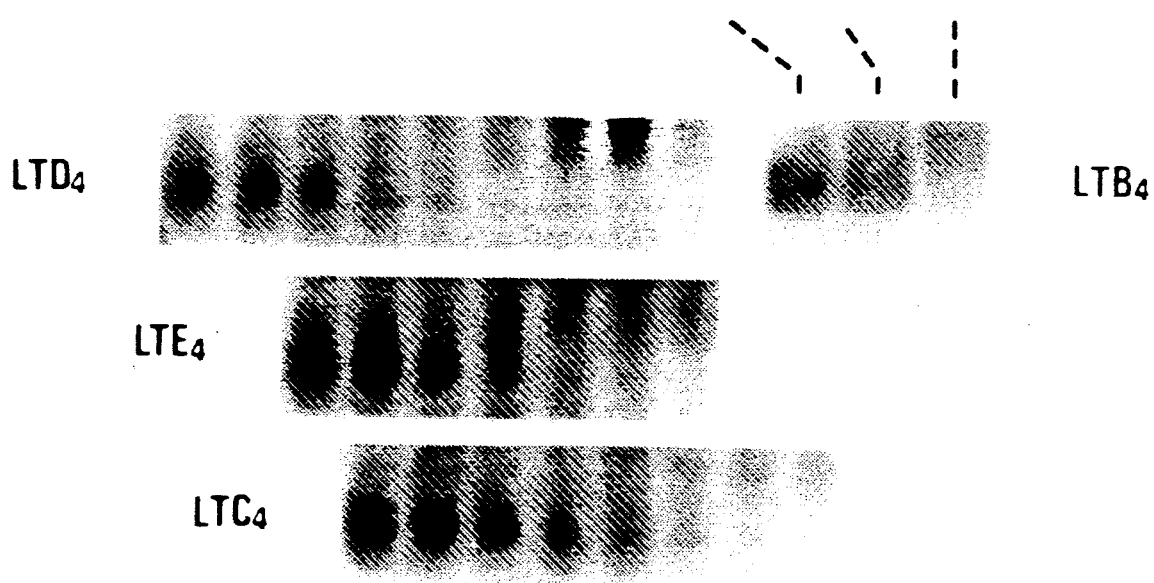
FIGS. 8(A)-8(C) Competition for [$^3$H]LTD$_4$ and [$^{125}$I]Azido-LTD$_4$ specific binding and [$^{125}$I]Azido-LTD$_4$ photolabelling of the 45 kDa protein by leukotrienes. [$^3$H]LTD$_4$ and [$^{125}$I]Azido-LTD$_4$ binding assays and [$^{125}$I]Azido-LTD$_4$ photoaffinity labelling of guinea-pig lung membranes were performed, as described in the Methods, in the presence of 0-100 nM LTD$_4$ (○) and LTE$_4$ ( ), 0-1000 nM LTC$_4$ (Δ) and 0-10 μM LTB$_4$ ( ). Binding assay results were expressed as the percentage of maximum specific binding as a function of leukotriene concentration and are shown in FIG. 8(A) for [$^3$H]LTD$_4$ specific binding and FIG. 8(B) for [$^{125}$I]Azido-LTD$_4$ specific binding. IC$_{50}$ values were determined as described in FIGS. 1(A) and 1(B)
Figure 8A:
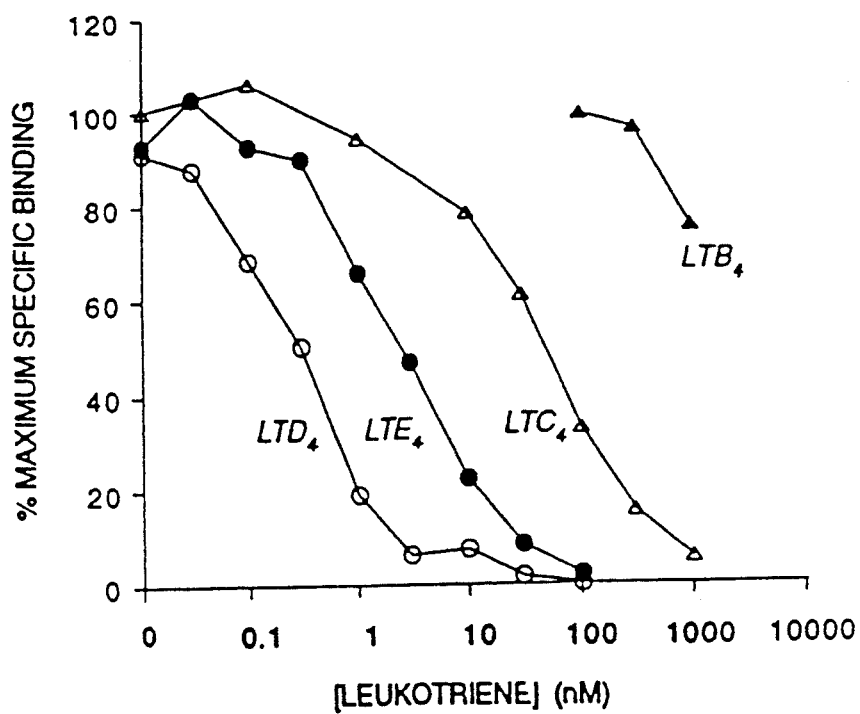
Figure 8B:
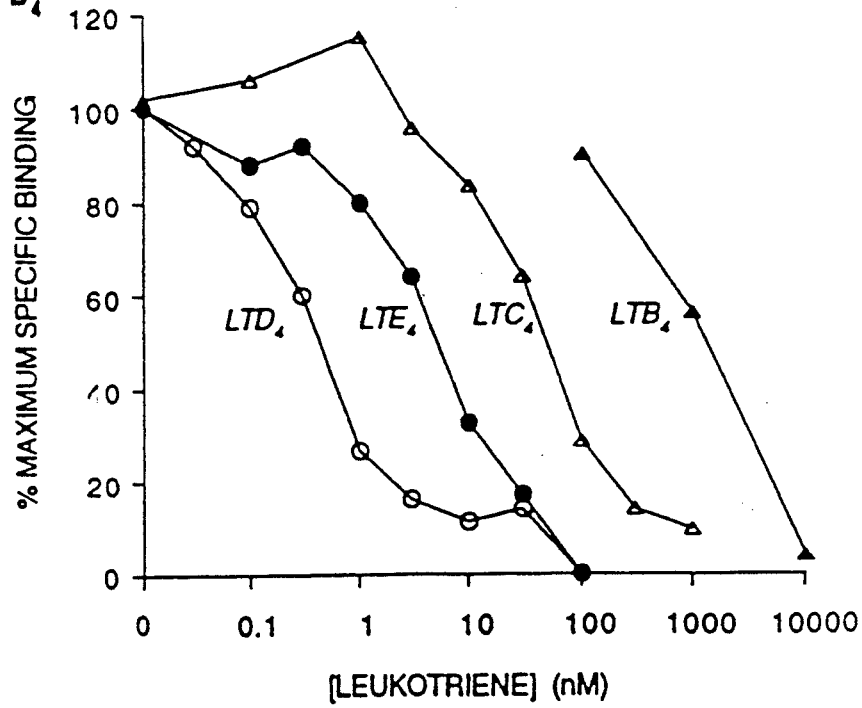

Photoaffinity Labelling of the 45 kDa Guinea-Pig Lung Membrane Protein by [$^{125}$I]Azido-LTD$_4$: Competition by Leukotriene D$_4$-Receptor Agonists and Antagonists The peptidyl leukotrienes, LTC$_4$, LTD$_4$ and LTE$_4$, were able to complete for both [$^3$H]LTD$_4$ and [$^{125}$I]Azido-LTD$_4$ specific binding to guinea-pig lung membranes with the same rank order of potency, displaying almost identical IC$_{50}$ values, FIGS. 8(A) and 8(B). LTD$_4$ was the most potent ligand when competing for both [$^3$H]LTD$_4$ and [$^{125}$I]Azido-LTD$_4$ specific binding, with IC$_{50}$ values of 0.3 nM and 0.4 nM respectively. LTE$_4$ was 10-fold less potent then LTD$_4$ in both cases, while LTC$_4$ was the least effective of the peptidyl leukotrienes, displaying an IC$_{50}$ value of approximately 50 nM against both [$^3$H]LTD$_4$ and [$^{125}$I]Azido-LTD$_4$ specific binding sites. The non-peptidyl LTB$_4$ was the least effective competing agonist, being approximately 10000-fold less active than LTD$_4$. The selective [$^{125}$I]Azido-LTD$_4$ photolabelling of the 45 kDa guinea-pig lung membrane protein was inhibited by leukotrienes with the same rank order of potency as demonstrated in the competition binding assays with LTD$_4$>LTD$_4$>LTC$_4$>>LTB$_4$, FIG. 8(C). In addition, the IC$_{50}$ values for leukotriene inhibition determined by laser densitometry of the radiolabelled 45 kDa protein corresponded to the IC$_{50}$ values from the competition curves, being 0.4 nM for LTD$_4$, 5 nM for LTE$_4$ and 50 nM for LTC$_4$. In agreement with the radioreceptor binding assay data, LTB$_4$ was only able to compete for the selective radiolabelling of the 45 kDa protein at the relatively high concentration of 10 $\mu$M.

Figure 9A:
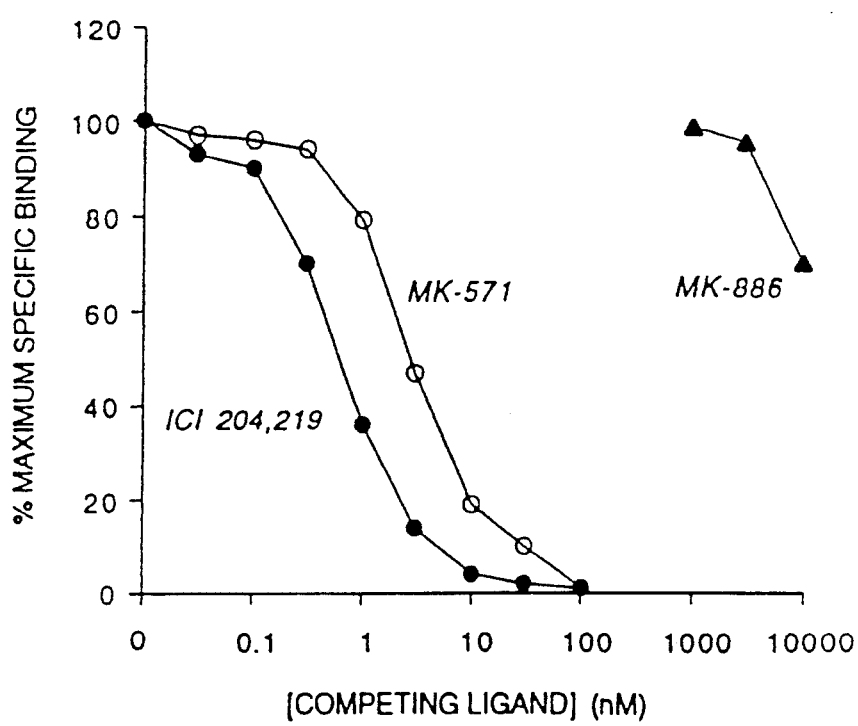
FIGS. 9(A)–9(C) Competition for [$^3$H]LTD$_4$ and [$^{125}$I]Azido-LTD$_4$ specific binding and [$^{125}$I]Azido-LTD$_4$ photolabelling of the 45 kDa protein by leukotriene D$_4$-receptor antagonists. [$^3$H]LTD$_4$ and [$^{125}$I]Azido-LTD$_4$ binding assays and [$^{125}$I]Azido-LTD$_4$ photoaffinity labelling of guinea-pig lung membranes were performed, as described in the Methods, in the presence of 0–100 nM MK-571 (○) and ICl 204,219 ( ) and 0–10 μM MK-886 ( ). Binding assay results were expressed as the percentage of maximum specific binding as a function of antagonist concentration and are shown in FIG. 9(A) for [$^3$H]LTD$_4$ specific binding and FIG. 9(B) for [$^{125}$I]Azido-LTD$_4$ specific binding. IC$_{50}$ values were determined as described in FIGS. 1(A) and 1(B)
Figure 9B:
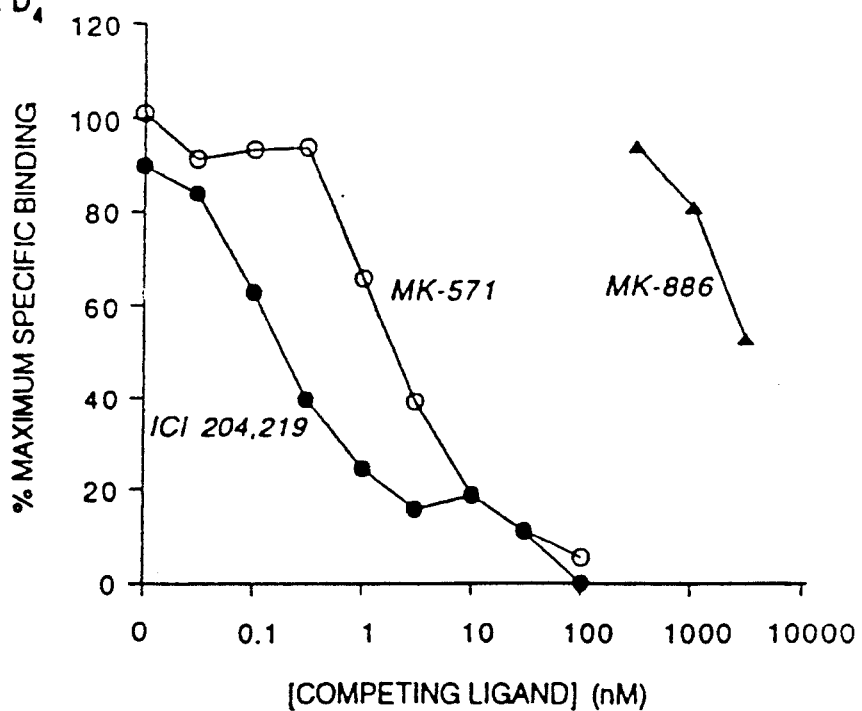
Figure 9C:
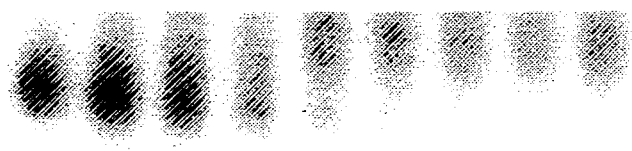
Figure 9C:
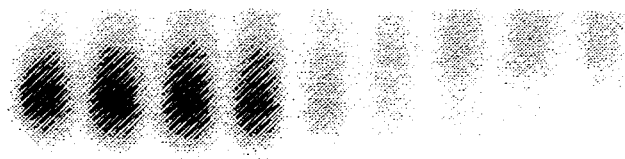
Figure 9C:
Figure 10:
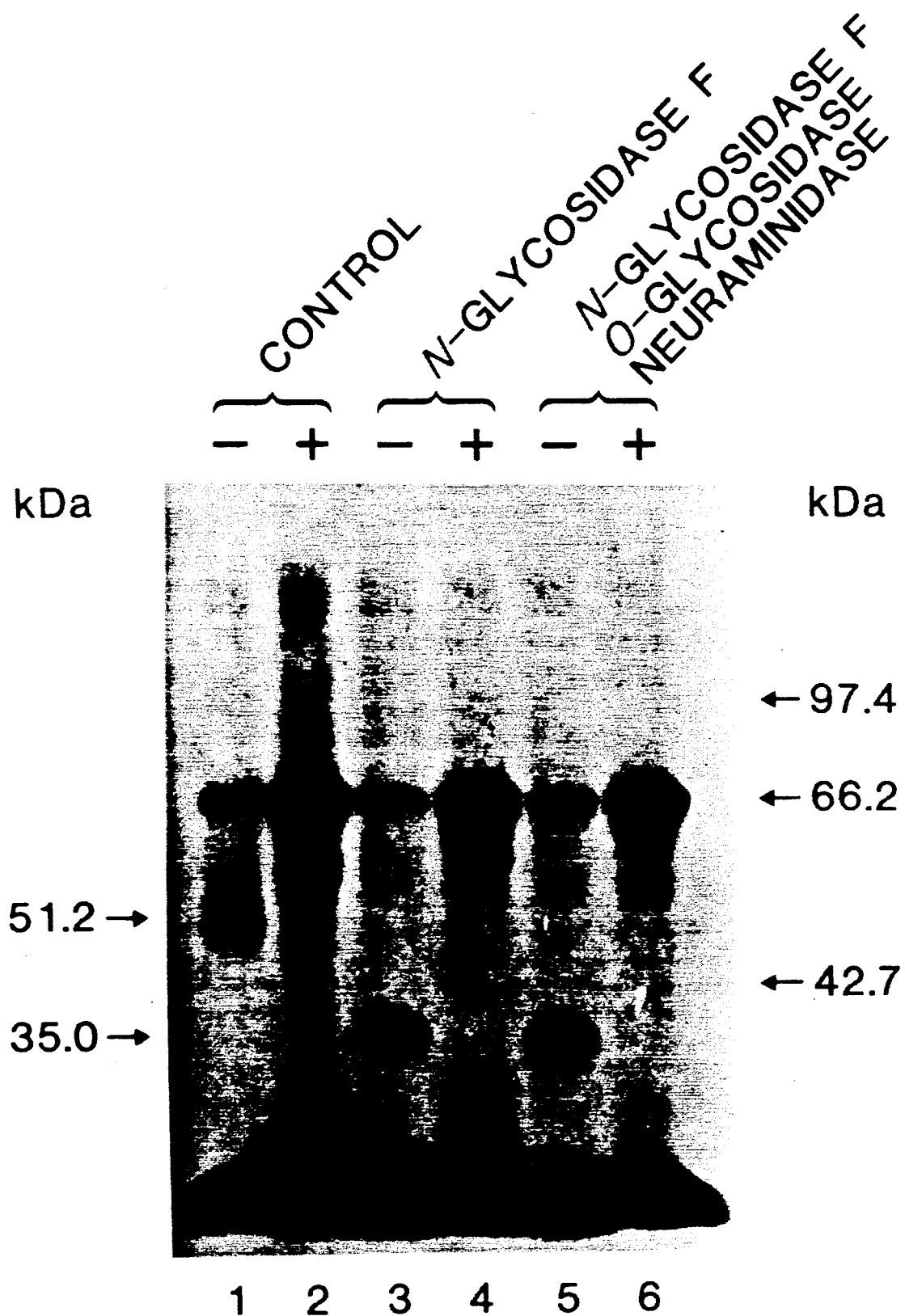
FIG. 10. Deglycosylation of the [$^{125}$I]Azido-LTD$_4$ photoaffinity labeled 45 kDa guinea-pig lung membrane protein by N-Glycosidase F. [$^{125}$I]Azido-LTD$_4$ photoaffinity labelling of guinea-pig lung membranes were performed, as described in the Methods, in the absence and presence of 1 μM LTD$_4$. Following photolysis the guinea-pig lung membranes were recovered from 1 ml sample aliquots by centrifugation at 150,000×g for 15 min at 4° C. The membranes were then solubilized in 20 μl of incubation buffer (20 mM NaHPO$_4$, pH 7.4, containing 10 mM EDTA and 1 % (v/v) 2-mercaptoethanol) containing 1 % (w/v) SDS. The solubilized preparation was then diluted with incubation buffer to a final volume of 200 μl containing 1 % (w/v) octylglucoside and 0–60 U / ml of recombinant N-Glycosidase F, and incubated overnight at room temperature. Samples were further diluted in 3-fold concentrated SDS sample buffer and analysed by SDS-PAGE, followed by autoradiography. The resulting autoradiograph shows the profile of radiolabelled guinea-pig lung membrane proteins in the non-digested control, Lanes A (−LTD$_4$) and B (+LTD$_4$) and following digestion with 60 U / ml of recombinant N-Glycosidase F, Lanes C (−LTD$_4$) and D (+LTD$_4$). The migration of the molecular weight standards is indicated on the left.

In a comparable series of competition experiments the LTD$_4$-receptor anagonists MK-571 and lCl 204,219 were shown to compete for both [$^3$H]LTD$_4$ and [$^{125}$I]Azido-LTD$_4$ specific binding to guinea-pig lung membranes with nanomolar potency. The quinoline MK-571 displayed comparable lC$_{50}$ values of 2 nM and 3 nM against [$^3$H]LTD$_4$ and [$^{125}$I]Azido-LTD$_4$ specific binding. The lC$_{50}$ values obtained for inhibition of [$^3$H]LTD$_4$ and [$^{125}$I]Azido-LTD$_4$ specific binding by the indole lCl 204,219 were also similar, being 0.2 nM and 0.6 nM, FIGS. 9(A) and 9(B). The ability of these antagonists to inhibit the selective [$^{125}$I]Azido-LTD$_4$ photolabelling of the 45 kDa guinea-pig lung membrane protein was found agree with their potency in equilibrium binding competition assays, FIG. 9(C). The lC$_{50}$ values determined by laser densitometry of the radiolabelled 45 kDa protein were 1 nM for MK-571 and 0.3 nM for lCl 204,219. Similar studies were performed using the leukotriene biosynthesis inhibitor MK-886. This compound was found to be a weak competing ligand for both [$^3$H]LTD$_4$ and [$^{125}$I]Azido-LTD$_4$ specific binding, producing inhibition at concentrations >1 $\mu$M. In agreement with the equilibrium binding data, MK-886 was only able to compete for the selective radiolabelling of the 45 kDa protein at similarly high ligand concentrations, FIGS 9(A), 9(B) and 9(C).

Deglycosylation of the [$^{125}$I]Azido-LTD$_4$ photoaffinity labeled 45 kDa guinea-pig lung membrane protein by N-Glycosidase F

[$^{125}$I]Azido-LTD$_4$ photoaffinity labelled guinea-pig lung membrane proteins were digested with N-Glycosidase F. Treatment with N-Glycosidase F resulted in the disappearance of the selectively radiolabelled 45 kDa protein and the appearance of a selectively radiolabelled protein with an apparent M$_r$ of 40000. The radiolabelled precursor and the resulting product were not present in samples pretreated with 1 $\mu$M LTD4. Complete digestion of the 45 kDa protein was achieved at each N-Glycosidase F concentration tested over the range 0.06–6 U/ml. In every case the only detectable product was the 40 kDa protein. These data are consistent with the hyposthesis that the selectively radiolabelled 45 kDa protein is glycosylated at asparagine residues and that removal of the N-glycans liberates a 40 kDa protein. This is also supported by qualitative evidence since the radiolabelled precursor migrated as a diffuse band during SDS-PAGE, behaviour typical of glycoproteins, while the deglycosylated product migrated as a more focused band. [$^{125}$I]azido-LTD$_4$ is useful as a probe for binding to the LTD$_4$ receptor and for the purification thereof.

The 45 kD protein, i.e. the LTD$_4$ receptor, is useful for binding to LTD$_4$ antagonists, e.g. in identifying compounds which could be used to treat LTD$_4$ mediated disease states, such as asthma. The protein can also be used therapeutically as a competitive binder of LTD$_4$.

REFERENCES

Augstein, J., J. B. Farmer, T. B. Lee, P. Sheard and M. L. Tattersall, 1973, Selective inhibitor of slow reacting substance of analphylaxis, Nature 245, 215.

Aharony, D. and R. C. Falcone, 1989, Binding of $^3$H-LTD$_4$ and the peptide leukotriene antagonist $^3$H-ICI 198,615 to receptors on human lung membranes, in Leukotrienes and prostanoids in health and disease. New Trends Lipid Mediators Res. (Editors Zor U, Z. Naor and A. Danon), 3, 67.

Birnbaumer, L., 1990, G proteins in signal transduction, Ann. Rev. Pharmacol. Toxicol., 30, 675.

Boucheloche, P. N. and D. Berild, 1991, Possible existence of leukotriene D$_4$ receptors and mechanism of their signal transduction in human polymorphonuclear leukocytes, Scand. J. Lab. Invest. 51, Suppl. 204, 47.

Bruns, R. F., W. J. Thomsen, and T. A. Pugsley, 1983, Binding of leukotriene C$_4$ and D$_4$ to membranes from guinea pig lung: regulation by ions and guanine nucleotides, Life Sciences 33, 645.

Buckner, C. K., R. D. Krell, R. B. Laravuso, D. B. Coursin, P. R. Bernstein and J. A. Will, 1986, Pharmacological evidence that human intralobar airways do not contain different receptors that mediate contractions to leukotriene C$_4$ and leukotriene D$_4$, J. Pharmacol. Experimental Therapeutics, 237, 558.

Crooke, S. T., M. Mattern, H. M. Sarau, J. D. Winkler, J. Balcarek, A. Wong and C. F. Bennett, 1989, The signal transduction system of the leukotriene D$_4$ receptor, TIPS Reviews 10, 103.

Harris, P. and P. Ralph, 1985, Human leukemic models of myelomonocytic development: a review of the HL-60 and U937 cell lines, J. Leukocyte Biology, 37, 407.

Hendeles, L., D. Davison, K. Blake, E. Harmon, R. Cooper and D. Margolskee, 1990, Leukotriene D$_4$ is an important mediator of antigen-induced bronchoconstriction: attenuation of dual response with MK-571, a specific leukotriene D$_4$ receptor antagonist. J. Allergy Clin. Immunol. 85, 197.

Huber, M. and D. Keppler, 1987, Inhibition of Leukotriene D$_4$ catabolism by D-penicillamine, Eur. J. Biochem. 167, 73.

Jones, T. R., C. Davis and E. E. Daniel, 1982, Pharmacological study of the contractile activity of leukotriene C$_4$ and D$_4$ on isolated human airway smooth muscle, Can. J. Pharm. Physiol. 60, 638.

Jones, T. R., R. Zamboni, M. Belley, E. Champion, L. Charette, A. W. Ford-Hutchinson, R. Frenette, J.-Y. Gauthier, S. Leger, P. Masson, C. S. McFarland, H. Piechuta, J. Rokach, H. Williams, R. N. Young, R. N. DeHaven and S. S. Pong, 1989, Pharmacology of L-660,711 (MK-571): a novel potent and selective leukotriene D$_4$ receptor antagonist, Can. J. Physiol. Pharmacol. 67, 17.

Kips, J. C., G. Joos, D. Margolskee, I. Delepeleire, J. D. Rogers, R. Pauwels and M. Van Der Straeten, 1989a, L-660,711: A potent antagonist of LTD$_4$-induced bronchoconstriction in man, Am. Rev. Res. Dis. 139, A63.

Kips, J. C., G. Joos, Margolskee, I. Delepeleire, R. Pauwels and M. Van Der Straeten, 1989b, MK-571 (L-660,711) A potent leukotriene D$_4$ antagonist in asthmatic men, Eur. Respir. J. 8 (Suppl): 789S.

Kips, J. C., D. Margolskee, I. Delepeleire, G. Joos, V. Williams, A. Buntinx and R. Pauwels, 1991, MK-0679 is a potent and selective LTD$_4$ antagonist in asthmatic men, Am. Rev. Res. Dis. 143, A599.

Lefkowitz, R. J., J. M. Stadel and M. G. Caron, 1983, Adenylate cyclase-coupled beta-adrenergic receptors: structure and mechanisms of activation and desensitization, Ann Rev. Biochem. 52, 159.

Lewis, M. A., S. Mong, R. L. Vessella and S. T. Crooke, 1985, Identification and characterization of leukotriene D$_4$ receptors in adult and fetal human lung, Biochem. Pharmacol. 34, 4311.

Mancini, J., G. Reid, E. Rands, R. Diehl, D. Miller, C. Rouzer, S. Kargman, R. Dixon, J. Evans and P. Vickers, 1991, Induction of 5-lipoxygenase-activating protein in DMSO-differentiated U937 cells, XIth Washington International Spring Symposium on Prostaglandins, leukotrienes, lipoxins and PAF, Abstract 124.

Manning P. J., R. M. Watson, D. J. Margolskee, V. C. Williams, J. I. Schwartz and P. O'Byrne, 1990, Inhibition of exercise-induced bronchoconstriction by MK-571, a potent leukotriene $D_4$ receptor antagonist, N. Eng. J. Med. 323, 1736.

Mattern, M. R., Mong, S.-M. Mong, J. O'Leary Bartus, H. M. Sarau, M. A. Clarke, J. J. Foley and S. T. Crooke, 1990, Transient activation of topoisomerase I in leukotriene $D_4$ signal transduction in human cells, Biochem. J. 265, 101.

McPherson, G. A., 1985, Analysis of radioligand binding experiments: a collection of computor programs for the IBM PC, J. Pharmacol. Methods 14, 213.

Metters, K. M., E. A. Frey and A. W. Ford-Hutchinson, 1991, Characterization of the leukotriene $D_4$ receptor in hyperreactive rat lung, Eur. J. Pharmacol. 194, 51.

Mong, S., H.-L. Wu, G. K. Hogaboom, M. A. Clark and S. T. Crooke, 1984, Characterization of the Leukotriene $D_4$ receptor in guinea-pig lung, Eur. J. Pharmacol. 102, 1.

Mong, S., H.-L. Wu, G. K. Hogaboom, M. A. Clark, J. M. Stadel and S. T. Crooke, 1985a, Regulation of ligand binding to leukotriene $D_4$ receptors: effects of cations and guanine nucleotides, Eur. J. Pharmacol. 106, 241.

Mong, S., M. O. Scott, M. A. Lewis, H.-L. Wu, G. K. Hogaboom, M. A. Clark and S. T. Crooke, 1985b, Leukotriene $E_4$ binds specifically to $LTD_4$ receptors in guinea pig lung membranes, Eur. J. Pharmacol. 109, 183.

O'Sullivan, B. P. and S. Mong, 1989, Binding of radiolabelled high affinity antagonist to leukotriene $D_4$ receptor in guinea pig lung membranes: Interconversion of agonist-receptor affinity states, Mol. Pharmacol., 35, 789.

Örning, L. and S. Hammerström, 1980, Inhibition of leukotriene C and leukotriene D biosynthesis, J. Biol. Chem. 255, 8023.

Piper, P. J., 1984, Formation and action of leukotrienes, Physiological Rev. 64, 744.

Pong, S.-S. and R. N. DeHaven, 1983a, Characterization of a leukotriene $D_4$ receptor in guinea pig lung, Proc. Natl. Acad. Sci. U.S.A. 80, 7415.

Pont, S.-S., R. N. DeHaven, F. A. Kuehl, Jr. and R. W. Egan, 1983b, Leukotriene $C_4$ binding to rat lung membranes, J. Biol. Chem. 258, 9616.

Rosenthal, H. D., 1967, A graphic method for the determination and presentation of binding parameters in a complex system, Anal. Biochem. 20, 525.

Rovati, G. E., D. Oliva, D., L. Sautebin, G. C. Folco, A. F. Welton and S. Nicosia, 1985, Identification of specific binding sites for leukotriene $C_4$ in membranes from human lung, Biochem. Pharmacol., 34, 2831.

Samuelsson, B., 1983, Leukotrienes: Mediators of immediate hypersensitivity reactions and imflammation, Science 220, 568.

Sarau, H. M. and S. Mong, 1989, Co-expression of luekotriene $B_4$ and leukotriene $D_4$ receptors on human monocytic leukemia U-937 cells, in Advances in Prostoglandin, Thromboxane, and Leukotriene Research (Editors Samuelsson, B., P.Y.-K. Wong and F. F. Sun) Raven Press, New York, 19, 180.

Saussy, D. L., H. M. Sarau, J. J. Foley, S. Mong and S. T. Crooke, 1989, Mechanisims of leukotriene $E_4$ partial agonist activity at leukotriene $D_4$ receptors in differentiated U-937 cells, J. Biol. Chem. 264, 19845.

Scatchard, G., 1949, The attraction of proteins for small molecules and ions, Ann. N.Y. Acad. Sci. 51, 660.

Shaw, A. and R. D. Krell, 1991, Peptide leukotrienes: Current status of research, J. Med. Chem., 34, 1235.

Simonson, M. S., P. Mené, G. R. Dubyak and M. J. Dunn, 1988, Identification and transmembrane signaling of leukotriene $D_4$ receptors in human mesangial cells, American J. Physiology, 255, C771.

Sjölander, A., E. Grönroos, S. Hammarström and T. Andersson, 1990?, Leukotriene $D_4$ and $E_4$ induce transmembrane signaling in human epithelial cells. Single cell analysis reveals diverse pathways at the G-protein level for the influx and the intracellular mobilization of $Ca^{2+}$, J. Biol. Chem., 265, 20976.

Sun, F. E., L.-Y. Chau, B. Spur, E. J. Corey, R. A. Lewis and K. F. Austen, 1986, Identification of a high affinity leukotriene $C_4$ binding protein in rat liver cytosol as glutathione-S-transferase, J. Biol. Chem., 261, 8540.

Sundström C. and K. Nilsson, 1976, Establishment and characterization of a histiocytic lymphoma cell line (U-937), Ind. J. Cancer, 17, 565.

Synder, D. W., R. E. Giles, R. A. Keith, Y, K. Yee, and R. D. Krell, 1987, The in vitro pharmacology of ICI 198615: A novel, potent and selective leukotriene antagonist, J. Pharmacol. Exp. Ther., 243, 548.

Tate, S. S. and A. Meister, 1978, Serine-borate complex as a transition-state inhibitor of γ-glutamyl transpeptidase, Proc. Natl. Acad. Sci. USA 75, 4806.

Taylor, I. K., K. M. O'Shaughnessy, R. W. Fuller and C. T. Dollery, 1991, Effect of cysteinyl-leukotriene (LT) receptor antagonist ICI 204,219 on allergen-induced bronchoconstriction and airway hyper-reactivity in atopic subjects, Am. Rev. Res. Dis. 143, A599.

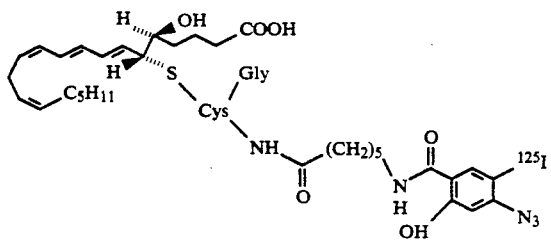

What is claimed is:

1. The $LTD_4$ receptor, which is a 45 kD protein, as determined by SDS-PAGE, bound to [$^{125}I$]azido of the formula: